US009656001B2

(12) United States Patent
Mayes et al.

(10) Patent No.: US 9,656,001 B2
(45) Date of Patent: *May 23, 2017

(54) ANTI-ADHESIVE BARRIER MEMBRANE USING ALGINATE AND HYALURONIC ACID FOR BIOMEDICAL APPLICATIONS

(71) Applicant: BOARD OF REGENTS, THE UNIVERSITY OF TEXAS SYSTEM, Austin, TX (US)

(72) Inventors: Sarah Mayes, Austin, TX (US); Christine E. Schmidt, Gainesville, FL (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/803,258

(22) Filed: Jul. 20, 2015

(65) Prior Publication Data

US 2016/0015866 A1 Jan. 21, 2016

Related U.S. Application Data

(63) Continuation of application No. 13/269,344, filed on Oct. 7, 2011, now Pat. No. 9,095,558.

(60) Provisional application No. 61/391,299, filed on Oct. 8, 2010.

(51) Int. Cl.
*A61L 31/04* (2006.01)
*A61K 31/192* (2006.01)
*A61K 31/195* (2006.01)
*A61L 31/14* (2006.01)
*A61L 31/16* (2006.01)

(52) U.S. Cl.
CPC .......... *A61L 31/041* (2013.01); *A61K 31/192* (2013.01); *A61K 31/195* (2013.01); *A61L 31/145* (2013.01); *A61L 31/148* (2013.01); *A61L 31/16* (2013.01); *A61L 2300/414* (2013.01); *A61L 2300/43* (2013.01); *A61L 2300/62* (2013.01)

(58) Field of Classification Search
CPC .... A61L 31/041; A61L 31/145; A61L 31/148; A61L 31/16; A61L 2300/414; A61L 2300/43; A61L 2300/62; A61K 31/192; A61K 31/195
See application file for complete search history.

(56) References Cited

U.S. PATENT DOCUMENTS

| | | |
|---|---|---|
| 4,141,973 A | 2/1979 | Balazs |
| 4,818,542 A | 4/1989 | DeLuca |
| 4,937,270 A | 6/1990 | Hamilton |
| 5,017,229 A | 5/1991 | Burns |
| 5,531,716 A | 7/1996 | Luzio |
| 5,531,735 A | 7/1996 | Thompson |
| 5,563,186 A | 10/1996 | Thompson |
| 5,622,707 A | 4/1997 | Dorigatti |
| 5,714,166 A | 2/1998 | Tomalia |
| 5,750,585 A | 5/1998 | Park |
| 5,760,200 A | 6/1998 | Miller |
| 5,863,551 A | 1/1999 | Woerly |
| 5,919,442 A | 7/1999 | Yin |
| 5,939,323 A | 8/1999 | Valentini |
| 6,007,833 A | 12/1999 | Chudzik |
| 6,030,958 A | 2/2000 | Burns |
| 6,060,534 A | 5/2000 | Ronan |
| 6,096,018 A | 8/2000 | Luzio |
| 6,124,273 A | 9/2000 | Drohan |
| 6,133,325 A | 10/2000 | Schwartz et al. |
| 6,156,572 A | 12/2000 | Bellamkonda |
| 6,174,999 B1 | 1/2001 | Miller |
| 6,184,266 B1 | 2/2001 | Ronan |
| 6,235,726 B1 | 5/2001 | Burns |
| 6,271,278 B1 | 8/2001 | Park |
| 6,294,202 B1 | 9/2001 | Burns |
| 6,334,968 B1 | 1/2002 | Shapiro |
| 6,368,356 B1 | 4/2002 | Zhong |
| 6,372,244 B1 | 4/2002 | Antanavich |
| 6,387,978 B2 | 5/2002 | Ronan |
| 6,410,044 B1 | 6/2002 | Chudzik |
| 6,425,918 B1 | 7/2002 | Shapiro |
| 6,500,777 B1 | 12/2002 | Wiseman |

(Continued)

FOREIGN PATENT DOCUMENTS

| | | | | |
|---|---|---|---|---|
| EP | 1806367 | * | 11/2007 | ......... A61K 47/4823 |
| JP | 06100468 | | 9/1992 | |

(Continued)

OTHER PUBLICATIONS

Daniel Kohane & Robert Langer, Polymeric Biomaterials in Tissue Engineering, 63 Ped. Res. 487 (2008).*
Jejurikar A, et al. "A novel strategy for preparing mechanically robust ionically cross-linked alginate hydrogels." Biomed. Mater. 6 (2011) 025010 (12pp).
Kang H, et al. "An effect of alginate on the stability of LDH nanosheets in aqueous solution and preparation of alginate/LDH nanocomposites." Carbohydrate Polymers 100 (2014) 158-165.
Liverani L, et al. "Simple fabrication technique for multilayered stratified composite scaffolds suitable for interface tissue engineering." Materials Science & Engineering A 557 (2012) 54-58.
Gleghorn JP, et al. "Adhesive properties of laminated alginate gels for tissue engineering of layered structures." J Biomed Mater Res 85A: 611-618, 2008.
Haidar ZS, et al. "Protein release kinetics for coreeshell hybrid nanoparticles based on the layer-by-layer assembly of alginate and chitosan on liposomes." Biomaterials 29 (2008) 1207-1215.

(Continued)

*Primary Examiner* — Sean Basquill
(74) *Attorney, Agent, or Firm* — Trop, Pruner & Hu, P.C.

(57) ABSTRACT

A non-synthetic, hydrophilic, biodegradable, biocompatible polysaccharide based non-toxic anti-adhesion hydrogel barrier is disclosed herein. The barrier of the present invention is formed by constructing a unique interpenetrating, cross-linked network with a unique porosity. Furthermore, the barrier of the present invention is comprised of tunable biopolymers for controllable mechanical robustness and degradation. The barrier of the present invention effectively reduces unwanted adhesions using non-synthetic components.

8 Claims, 11 Drawing Sheets

(56) References Cited

U.S. PATENT DOCUMENTS

| | | | |
|---|---|---|---|
| 6,511,650 B1 | 1/2003 | Eiselt | |
| 6,521,223 B1 | 2/2003 | Calias | |
| 6,548,081 B2 | 4/2003 | Sadozai | |
| 6,565,878 B2 * | 5/2003 | Schoenfeldt | A61L 15/28 424/424 |
| 6,566,345 B2 | 5/2003 | Miller et al. | |
| 6,599,526 B2 | 7/2003 | Dimitrijevich | |
| 6,600,011 B2 | 7/2003 | McDonnell | |
| 6,608,117 B1 | 8/2003 | Gvozdic | |
| 6,610,669 B1 | 8/2003 | Calias | |
| 6,630,167 B2 | 10/2003 | Zhang | |
| 6,630,457 B1 | 10/2003 | Aeschlimann | |
| 6,638,917 B1 | 10/2003 | Li | |
| 6,642,363 B1 | 11/2003 | Mooney | |
| 6,653,240 B2 | 11/2003 | Crawford | |
| 6,653,420 B2 | 11/2003 | Domschke | |
| 6,693,089 B1 | 2/2004 | Li | |
| 6,703,041 B2 | 3/2004 | Burns | |
| 6,723,709 B1 | 4/2004 | Pressato | |
| 6,750,262 B1 | 6/2004 | Hahnle | |
| 6,767,928 B1 | 7/2004 | Murphy | |
| 6,793,675 B2 | 9/2004 | Shapiro | |
| 6,818,018 B1 | 11/2004 | Sawhney | |
| 6,841,153 B1 | 1/2005 | Chegini | |
| 6,869,938 B1 | 3/2005 | Schwartz | |
| 6,897,271 B1 | 5/2005 | Domschke | |
| 6,913,765 B2 | 7/2005 | Li | |
| 6,924,370 B2 | 8/2005 | Chudzik | |
| 6,939,562 B2 | 9/2005 | Spiro | |
| 6,943,154 B2 | 9/2005 | Miller | |
| 6,960,617 B2 | 11/2005 | Omidian | |
| 6,991,652 B2 | 1/2006 | Burg | |
| 7,022,313 B2 | 4/2006 | O'Connor | |
| 7,083,697 B2 | 8/2006 | Dao | |
| 7,201,917 B2 | 4/2007 | Malaviya | |
| 7,235,295 B2 | 6/2007 | Laurencin | |
| 7,347,988 B2 | 3/2008 | Hu | |
| 7,459,021 B2 | 12/2008 | Bukshpan | |
| 7,553,903 B2 | 6/2009 | Riegel | |
| 7,572,894 B2 | 8/2009 | Jin | |
| 7,629,388 B2 | 12/2009 | Mikos | |
| 7,682,540 B2 | 3/2010 | Boyan | |
| 7,741,476 B2 | 6/2010 | Lebreton | |
| 7,758,654 B2 | 7/2010 | Hoganson | |
| 7,919,542 B2 | 4/2011 | Hudgins | |
| 7,968,110 B2 | 6/2011 | Hubbard | |
| 7,988,992 B2 | 8/2011 | Omidian | |
| 7,989,505 B2 | 8/2011 | Hu | |
| 7,998,380 B2 | 8/2011 | Turng | |
| 8,025,901 B2 | 9/2011 | Kao et al. | |
| 8,110,242 B2 | 2/2012 | Hawkins | |
| 8,133,840 B2 | 3/2012 | Mika | |
| 8,323,675 B2 | 12/2012 | Greenawalt | |
| 9,095,558 B2 * | 8/2015 | Mayes | A61K 31/192 |
| 2002/0131933 A1 | 9/2002 | Delmotte | |
| 2003/0134132 A1 | 7/2003 | Winterton | |
| 2004/0138329 A1 | 7/2004 | Hubbell | |
| 2005/0107868 A1 | 5/2005 | Nakayama | |
| 2007/0031498 A1 | 2/2007 | Zong | |
| 2007/0202084 A1 | 8/2007 | Sadozai | |
| 2008/0069857 A1 | 3/2008 | Yeo | |
| 2008/0182012 A1 | 7/2008 | Fisher | |
| 2008/0264793 A1 | 10/2008 | Vigh | |
| 2008/0292664 A1 | 11/2008 | Giammona | |
| 2009/0062233 A1 | 3/2009 | Ji | |
| 2009/0081265 A1 | 3/2009 | Peppas | |
| 2009/0170973 A1 | 7/2009 | Mattiasson | |
| 2010/0062232 A1 | 3/2010 | Schauer | |
| 2010/0273667 A1 | 10/2010 | Kotov | |
| 2011/0008442 A1 | 1/2011 | Zawko | |
| 2012/0039959 A1 | 2/2012 | Tessmar | |
| 2012/0189760 A1 | 7/2012 | Steel | |
| 2012/0282302 A1 | 11/2012 | McCanless | |

FOREIGN PATENT DOCUMENTS

| | | | |
|---|---|---|---|
| JP | 04235124 | 5/1995 | |
| JP | 2000-271207 | 10/2000 | |
| JP | 2003062057 | 8/2001 | |
| JP | 2001212224 | 12/2001 | |
| JP | 2002-539855 | 11/2002 | |
| JP | 2006-006448 | 1/2006 | |
| JP | 2009529926 | 6/2009 | |
| JP | 2010-095586 | 4/2010 | |
| KR | 20020027747 A | 4/2002 | |
| KR | 20020032351 A | 5/2002 | |
| KR | 20030055102 A | 7/2003 | |
| WO | 9739737 | 10/1997 | |
| WO | WO 02/085419 | 10/2002 | |
| WO | 02092678 | 11/2002 | |
| WO | 2005020849 A2 | 10/2005 | |
| WO | 2009108760 | 9/2009 | |
| WO | 2009108760 A2 | 9/2009 | |
| WO | WO2009/108760 | 9/2009 | A61K 9/06 |
| WO | WO 2009/108760 * | 2/2010 | C08B 37/84 |
| WO | WO 2012/048283 | 4/2012 | |

OTHER PUBLICATIONS

Rivero S, et al. "Composite and bi-layer films based on gelatin and chitosan." Journal of Food Engineering 90 (2009) 531-539.

Thu HE, & Ng SF. "Gelatine enhances drug dispersion in alginate bilayer film via the formation of crystalline microaggregates." International Journal of Pharmaceutics 454 (2013) 99-106.

Patel VM, et al. "Mucoadhesive Bilayer Tablets of Propranolol Hydrochloride." AAPS PharmSciTech 2007; 8 (3) Article 77.

Cook MT, et al. "Layer-by-layer coating of alginate matrices with chitosan—alginate for the improved survival and targeted delivery of probiotic bacteria after oral adminstration." J. Mater. Chem. B, 2013, 1, 52.

Fioramonti SA, et al. "Multilayer emulsions as a strategy for linseed oil microencapsulation: Effect of pH and alginate concentration." Food Hydrcolloids 43 (2015) 8e17.

Zhang T, et al. "Pectin/lysozyme bilayers layer-by-layer deposited cellulose nanofibrous mats for antibacterial application." Carbohydrate Polymers 117 (2015) 687-693.

Boulmedais F, et al. "Polyelectrolyte multilayer films with pegylated polypeptides as a new type of anti-microbial protection for biomaterials." Biomaterials 25 (2004) 2003-2011.

The DP, et al. "Moisture barrier, wetting and mechanical properties of shellac/agar or shellac/cassava starch bilayer bio-membrane for food applications." Journal of Membrane Science 325 (2008) 277-283.

Morch, YRR A., et al., "Effect of Ca2+, Ba2+, and Sr2+ on Alginate Microbeads," Biomacromolecules, Trieste, Italy, Mar. 2006, 10 pages.

Cabodi, Mario, et al., "A Microfluidic Biomaterial," JACS (J. Am. Chem. Soc.) Communications, Ithaca, New York, 2005, 2 pages.

Supplemental European Search Report for PCT/US2011/055469 mailed Feb. 27, 2014.

International Search Report and Written Opinion for PCT/US2011/055461, dated Dec. 1, 2011, 10 pages.

Lindenhayn, K., et al., "Retention of Hyaluronic Acid in Alginate Beads: Aspects for in vitro Cartilage Engineering," J. Biomed. Mater. Res., (1999), vol. 44, pp. 149-155.

Masters, Kristyn S., et al., "Designing Scaffolds for Valvular Interstitial Cells: Cell Adhesion and Function on Naturally Derived Materials," J. Biomed. Mater Res. 71A, (2004), pp. 172-180.

Miralles, G., et al., "Sodiom Alginate Sponges With or Without Sodium Hyaluronate: In Vitro Engineering of Cartilage," J. Biomed. Mater. Res., (2001), vol. 57, pp. 268-278.

Zawko, Scott A., et al., "Crystal Templating Dendritic Pore Networks and Fibrillar Microstructure into Hydrogels," Acta Biomaterials, (2010), vol. 6, pp. 2415-2421.

Bekkers, John M., et al., "Targeted Dendrotomy Reveals Active and Passive Contributions of the Dendritic Tree to Synaptic Integration and Neuronal Output," PNAS, Jul. 3, 2007, vol. 104, No. 27, pp. 11447-11452.

(56) References Cited

OTHER PUBLICATIONS

Brisken, Cathrin, et al., "Alveolar and Lactogenic Differentiation," J. Mammary Gland Biol. Neoplasia, (2006), 11:239-248.
Chung, Cindy, et al., "Effects of Auricular Chondrocyte Expansion on Neocartilage Formation in Photocrosslinked Hyaluronic Acid Networks," Tissue Eng., Sep. 2006, 12(9):2665-2673.
Duffy, David C., et al., "Rapid Prototyping of Microfluidic Systems in Poly(dimethylsiloxane)," Anal. Chem., (1998), 70:4974-4984.
International Search Report and Written Opinion for PCT/US2009/035257, dated Oct. 12, 2009, 12 pages.
Khademhosseini, Ali, et al., "Microscale Technologies for Tissue Engineering and Biology," PNAS, Feb. 21, 2006, vol. 103, No. 8, pp. 2480-2487.
King, Kevin R., et al., "Biodegradable Microfluidics," Adv. Mater., Nov. 18, 2004, vol. 16, No. 22, pp. 2007-2012.
Larina, Olga, et al., "Ca2+ Dynamics in Salivary Acinar Cells: Distinct Morphology of the Acinar Lumen Underlies Near-Synchronous Global Ca2+ Responses," Journal of Cell Science, 118:4131-4139.
Leach, Jennie Baier, et al., "Photocrosslinked Hyaluronic Acid Hydrogels: Natural, Biodegradable Tissue Engineering Scaffolds," Biotechnol. Bioeng. 82:578-259.
Ma, Peter X., et al., "Biodegradable Polymer Scaffolds with Well-Defined Interconnected Spherical Pore Network," Tissue Engineering, vol. 7, No. 1, (2001), pp. 23-39.
Oaki, Yuya, et al., "Experimental Demonstration for the Morphological Evolution of Crystals Grown in Gel Media," Crystal Growth & Design, Jun. 27, 2003, vol. 3, No. 5, pp. 711-716.
Peppas, N.A., et al., "Hydrogeis in Pharmaceutical Formulations," European Journal of Pharmaceutics and Biopharmaceutics, (2000), 50, pp. 27-46.
Shah, Mita M., et al., "Branching Morphogenesis and Kidney Disease," Development 131, (2004), pp. 1449-1462.
Tsang, Valerie Liu, et al., "Fabrication of 3D Hepatic Tissues by Additive Photopatterning of Cellular Hydrogels," The FASEB Journal, (2007), 21, pp. 790-801.
Uludag, Hasan, et al., "Technology of Mammalian Cell Encapsulation," Advanced Drug Delivery Reviews, (2000), 42:29-64.
Xu, An-Wu, et al., "Biomimetic Mineralization," J. Mater. Chem., (2007), 17, pp. 415-449.
Yang, Shoufeng, et al., "The Design of Scaffolds for Use in Tissue Engineering. Part II. Rapid Prototyping Techniques," Tissue Engineering, (2002), vol. 8, No. 1, 11 pages.
Cho, W.J., et al. "Alginate Film as a Novel Post-Surgical Tissue Adhesion Barrier", Journal of Biomaterials Science-Polymer Edition, 21 (6-7), p. 701-713, 2010.
Oerther, S., et al. "Hyaluronate-Alginate Gel As A Novel Biomaterial: Mechanical Properties and Formation Mechanism", Biotechnology Bioeng., 63, 2006-215, 1999.
Oerther, S., et al., "High Interaction Alginate-Hyaluronate Associations by Hyaluronate Deacetylation for the Preparation of Efficient Biomaterials," Biopolymers, 54: 273-281, 2000.
U.S. Appl. No. 12/919,667, filed Aug. 26, 2010, entitled "Dendritic Macroporous Hydrogels Prepared by Crystal Templating" by Scott Zawko.
U.S. Appl. No. 13/269,366, filed Oct. 7, 2011, entitled "One-Step Processing of Hydrogels for Mechanically Robust and Chemically Desired Features" by Sarah Mayes.
W.M. Parks & Y.B. Guo, A Casting Based Process to Fabricate 3D Alginate Scaffolds and to Investigate the Influence of Heat Transfer on Pore Architecture During Fabrication, 28 Mat. Sci. Eng. C 1435 (2008).
Huang, "Rapid Fabrication of Bio-inspired 3D Microfluidic Vascular Networks", Advanced Materials, Jul. 10, 2009, 3567-3571, vol. 21, WILEY-VCH, Weinheim.
Depierro, "Influence of Polymerization Conditions on Nanostructure and Properties of Polyacrylamide Hydrogels Templated from Lyotropic Liquid Crystals", Chemical Materials, Oct. 18, 2006, 5609-5617, vol. 18, No. 23, American Chemical Society, Iowa City, Iowa.
Huang, "Rapid Fabrication of 3-D Branched Microvascular Flow Networks", Twelfth International Conference on Miniaturized Systems for Chemistry and Life Sciences, Oct. 12-16, 2008, 1435-1437, San Diego, California.
Seidel, "Synthesis of PolyHEMA Hydrogels for Using as Biomaterials. Bulk and Solution Radical-Initiated Polymerization Techniques", Materials Research, vol. 3, No. 3, Jul. 2000, 8 pages.
International Search Report and Written Opinion for PCT/US2011/055469, dated Jan. 12, 2011.
Japan Patent Office "Notice of Reasons for Rejection" in Japanese Application 2013-532995, Mailed on Jun. 30, 2015.
Japanese Intellectual Property Office "Final Rejection" mailed on Mar. 29, 2016 in application 2013-532995.

* cited by examiner

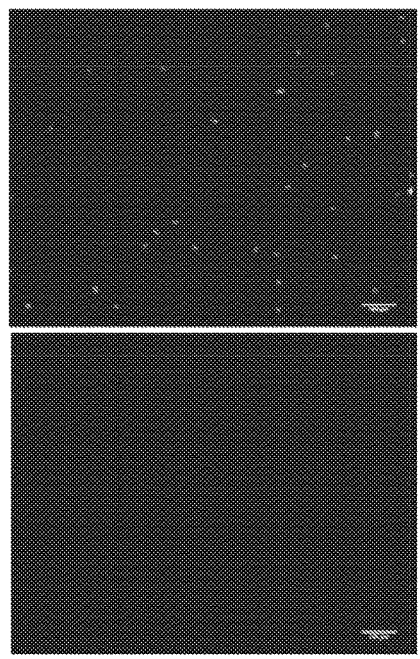
FIG. 9A
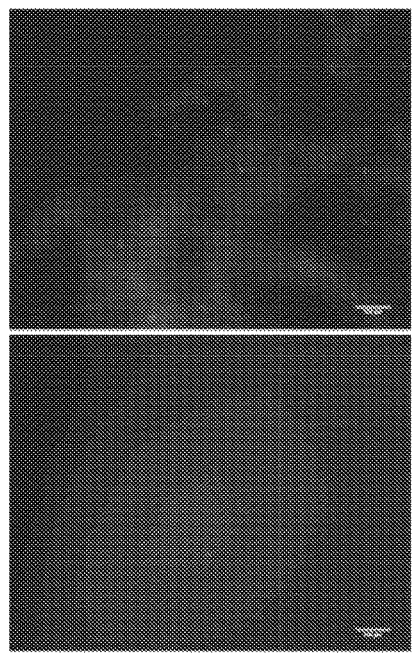
FIG. 9B
FIG. 9C
FIG. 9D

ANTI-ADHESIVE BARRIER MEMBRANE USING ALGINATE AND HYALURONIC ACID FOR BIOMEDICAL APPLICATIONS

CROSS-REFERENCE TO RELATED APPLICATIONS

This application is a continuation of U.S. patent application Ser. No. 13/269,344, filed Oct. 7, 2011 and entitled "Anti-Adhesive Barrier Membrane Using Alginate and Hyaluronic Acid for Biomedical Applications", which claims priority to U.S. Provisional Patent Application Ser. No. 61/391,299, filed Oct. 8, 2010. The content of each of the above applications is hereby incorporated by reference.

STATEMENT OF FEDERALLY FUNDED RESEARCH

This invention was made with government support under Grant no. BES0201744 and BES0500969 awarded by the National Science Foundation. The government has certain rights in this invention.

TECHNICAL FIELD OF THE INVENTION

The present invention relates in general to the field of biopolymers, and more particularly to a non-toxic, anti-adhesion hydrogel barrier comprising biocompatible polysaccharides.

INCORPORATION-BY-REFERENCE OF MATERIALS FILED ON COMPACT DISC

None.

REFERENCE TO A SEQUENCE LISTING

None.

BACKGROUND OF THE INVENTION

Without limiting the scope of the invention, its background is described in connection with the porous biopolymer hydrogels and methods of preparing the same.

WIPO Patent Publication No. WO 2009/108760 A8 (Zawko and Schmidt, 2009) discloses a hydrogel and a method of making a porous hydrogel by preparing an aqueous mixture of an uncrosslinked polymer and a crystallizable molecule; casting the mixture into a vessel; allowing the cast mixture to dry to form an amorphous hydrogel film; seeding the cast mixture with a seed crystal of the crystallizable molecule; growing the crystallizable molecule into a crystal structure within the uncrosslinked polymer; crosslinking the polymer around the crystal structure under conditions in which the crystal structure within the crosslinked polymer is maintained; and dissolving the crystals within the crosslinked polymer to form the porous hydrogel.

U.S. Patent Publication No. 20100209509 (Kao et al., 2010) discloses hydrogels wherein a polymer matrix is modified to contain a bifunctional poly(alkylene glycol) molecule covalently bonded to the polymer matrix. The hydrogels can be cross-linked using, for example, glutaraldehyde. The hydrogels may also be crosslinked via an interpenetrating network of a photopolymerizable acrylates. The hydrogels may also be modified to have pharmacologically-active agents covalently bonded to the poly(alkylene glycol) molecules or entrained within the hydrogel. Living cells may also be entrained within the hydrogels.

SUMMARY OF THE INVENTION

The present invention discloses a non-toxic anti-adhesion hydrogel barrier, composed of non-synthetic, hydrophilic, biodegradable, biocompatible polysaccharides formed by constructing a unique interpenetrating, crosslinked network with a unique porosity. The invention further describes a method for preparing the same.

In one embodiment the instant invention provides a method of making a porous anti-adhesion hydrogel comprising the steps of: (i) preparing an aqueous mixture of one or more uncrosslinked polymers and a crystallizable molecule, (ii) casting the aqueous mixture onto a vessel, a slide, a plate, tissue-culture dish or combinations and modifications thereof to form a cast mixture, (iii) drying the cast mixture to form an amorphous hydrogel film, (iv) seeding the cast mixture with a seed crystal of the crystallizable molecule, (v) growing the crystallizable molecule into a crystal structure within the uncrosslinked polymer, (vi) exposing the cast mixture to ultraviolet light, wherein the exposure results in a gelling or a crosslinking of the polymer, (vii) crosslinking the uncrosslinked polymer around the crystal structure by an addition of one or more crosslinking agents under conditions in which the crystal structure within the crosslinked polymer is maintained, (viii) removing the one or more crystals of the crystallizable polymers by rinsing with water to form the porous hydrogel and (ix) removing water from the porous hydrogel by controlled dessication under pressure. In one aspect of the method comprises the optional step of surface coating, modifying a surface or combinations thereof by soaking the dessicated hydrogel in an aqueous solution comprising the uncrosslinked polymer and one or more agents or chemicals to facilitate formation of one or more bonds. In another aspect the one or more bonds comprise ester bonds, amide bonds, carboxylate bonds, carbonyl bonds, ether bonds, imide bonds, and combinations and modifications thereof.

In yet another aspect of the method described hereinabove the polymer comprises nucleic acids, amino acids, saccharides, lipids and combinations thereof, in monomeric, dimeric, trimeric, oligomeric, multimeric, or polymeric forms. In another aspect the polymer is selected from the group consisting of collagen, chitosan, gelatin, pectins, alginate, hyaluronic acid, heparin and mixtures thereof. In a specific aspect the polymer comprises a non-synthetic biopolymer that is biodegradable, biocompatible and hydrophilic. In another aspect the polymer is gelled by a chemical crosslink, a physical crosslink, or a combination; wherein said crosslink is induced by an UV method, a temperature method, a pH method, an ion, or ion-radical based method or combinations thereof. In one aspect in the aqueous mixture comprises alginate and hyaluronic acid. In another aspect the crystallizable molecule comprises a small organic molecule selected from a salt, urea, beta cyclodextrin, glycine, and guanidine. In a specific aspect the crystallizable molecule comprises urea.

In one aspect the crosslinking agent selected from group consisting of calcium chloride, p-Azidobenzoyl hydrazide, N-5-Azido-2-nitrobenzoyloxsuccinimide, disuccinimidyl glutamate, dimethyl pimelimidate-(2)HCl, dimethyl suberimidate-2 HCl, disuccinimidyl suberate, bis[sulfosuccinimidyl suberate], 1-ethyl-3-[3-dimethylaminopropyl]carbodiimide-HCl, isocyanate, aldehyde, glutaraldehyde, paraformaldehyde and derivatives thereof. In another aspect the method comprises the optional step of encapsulation one or more agents selected from drugs, growth factors, hormones, proteins or combinations thereof in the one or more pores or the matrix of the porous hydrogel.

In another embodiment the instant invention discloses a directionally networked porous anti-adhesion hydrogel made by a method that comprises the steps of: i) preparing an aqueous mixture of one or more uncrosslinked polymers and a crystallizable molecule, ii) casting the aqueous mixture onto a vessel, a slide, a plate, tissue-culture dish or combinations and modifications thereof to form a cast mixture, iii) drying the cast mixture to form an amorphous hydrogel film, iv) seeding the cast mixture with a seed crystal of the crystallizable molecule, v) growing the crystallizable molecule into a crystal structure within the uncrosslinked polymer, wherein the crystal structure is networked, branched, and porous, vi) exposing the cast mixture to ultraviolet light, wherein the exposure results in a gelling or a crosslinking of the polymer, vii) crosslinking the uncrosslinked polymer around the crystal structure by an addition of one or more crosslinking agents under conditions in which the crystal structure within the crosslinked polymer is maintained, viii) removing the one or more crystals of the crystallizable polymers by rinsing with water to form the porous hydrogel, and ix) removing water from the porous hydrogel by controlled dessication under pressure.

The method disclosed hereinabove comprises the optional step of surface coating, modifying a surface or combinations thereof by soaking the dessicated hydrogel in an aqueous solution comprising the uncrosslinked polymer and one or more agents or chemicals to facilitate formation of one or more bonds. In one aspect the one or more bonds comprise ester bonds, amide bonds, carboxylate bonds, carbonyl bonds, ether bonds, imide bonds, and combinations and modifications thereof. In another aspect the polymer comprises nucleic acids, amino acids, saccharides, lipids and combinations thereof, in monomeric, dimeric, trimeric, oligomeric, multimeric, or polymeric forms. In yet another aspect the polymer is selected from the group consisting of collagen, chitosan, gelatin, pectins, alginate, hyaluronic acid, heparin and mixtures thereof.

In a related aspect the polymer comprises a non-synthetic polymer biopolymer, wherein the polymer is biodegradable, biocompatible and hydrophilic. In the method as described above the polymer is gelled by a chemical crosslink, a physical crosslink, or a combination; wherein said crosslink is induced by an UV method, a temperature method, a pH method, an ion, or ion-radical based method or combinations thereof. In one aspect the aqueous mixture comprises alginate and hyaluronic acid. In another aspect the crystallizable molecule comprises a small organic molecule selected from a salt, urea, beta cyclodextrin, glycine, and guanidine. In a specific aspect the crystallizable molecule comprises urea. In another aspect the crosslinking agent selected from group consisting of calcium chloride, p-Azidobenzoyl hydrazide, N-5-Azido-2-nitrobenzoyloxsuccinimide, disuccinimidyl glutamate, dimethyl pimelimidate-(2)HCl, dimethyl suberimidate-2 HCl, disuccinimidyl suberate, bis[sulfosuccinimidyl suberate], 1-ethyl-3-[3-dimethylaminopropyl]carbodiimide-HCl, isocyanate, aldehyde, glutaraldehyde, paraformaldehyde and derivatives thereof. In another aspect the method comprises the optional step of encapsulating one or more agents selected from drugs, growth factors, hormones, proteins or combinations thereof in the one or more pores or the matrix of the porous hydrogel. In yet another aspect the hydrogel prevents tissue adhesion following surgery, promotes wound healing, delivers drug or growth factors to the support healing, inhibits or prevents infiltration of blood, blood protein, fibroblasts, and inflammatory responses in the surgical site and is non-cytotoxic.

In yet another embodiment the present invention relates to a method of preventing tissue adhesion during or post-surgery in a patient comprising the steps of: identifying the patient in need of the prevention of tissue adhesion during or post-surgery amd administering an injectable solution of an anti-adhesion composition, wherein the composition comprises a non-cytotoxic, a non-immunogenic porous hydrogel, a film, a barrier or combinations and modifications thereof, prior to, during or after the surgery, wherein the composition is made by a method comprising the steps of: a) preparing an aqueous mixture of one or more uncrosslinked polymers and a crystallizable molecule, b) casting the aqueous mixture onto a vessel, a slide, a plate, tissue-culture dish or combinations and modifications thereof to form a cast mixture, c) drying the cast mixture to form an amorphous hydrogel film, d) seeding the cast mixture with a seed crystal of the crystallizable molecule, e) growing the crystallizable molecule into a crystal structure within the uncrosslinked polymer, f) exposing the cast mixture to ultraviolet light, wherein the exposure results in a gelling or a crosslinking of the polymer, g) crosslinking the uncrosslinked polymer around the crystal structure by an addition of one or more crosslinking agents under conditions in which the crystal structure within the crosslinked polymer is maintained, h) removing the one or more crystals of the crystallizable polymers by rinsing with water to form the porous hydrogel, and i) removing water from the porous hydrogel by controlled dessication under pressure.

In one aspect the method of making the porous hydrogel comprises the optional steps of, surface coating, modifying a surface or combinations thereof by soaking the dessicated hydrogel in an aqueous solution comprising the uncrosslinked polymer and one or more agents or chemicals to facilitate formation of one or more bonds and encapsulating one or more agents selected from drugs, growth factors, hormones, proteins or combinations thereof in the one or more pores or the matrix of the porous hydrogel, wherein the hydrogel provides a tunable or a controlled release of the one or more agents. In a specific aspect of the method the one or more agents comprise ibuprofen or tranexamic acid. In one aspect the composition the promotes wound healing, delivers drug or growth factors to the support healing, inhibits or prevents infiltration of blood, blood protein, fibroblasts, and inflammatory responses in the surgical site. In another aspect the polymer is a non-synthetic biodegradable, biocompatible and hydrophilic biopolymer. In a specific aspect the aqueous mixture comprises alginate and hyaluronic acid. In another aspect the crystallizable molecule comprises a small organic molecule selected from a salt, urea, beta cyclodextrin, glycine, and guanidine. In another aspect the crystallizable molecule comprises urea.

The present invention further discloses a composition for preventing tissue adhesion during or post-surgery in a patient comprising an injectable solution of an anti-adhesion composition, wherein the composition comprises a non-cytotoxic, a non-immunogenic porous hydrogel, a film, a barrier or combinations and modifications thereof. The composition of the present invention is made by a method comprising the steps of: i) preparing an aqueous mixture of one or more uncrosslinked polymers and a crystallizable molecule, ii) casting the aqueous mixture onto a vessel, a slide, a plate, tissue-culture dish or combinations and modifications thereof to form a cast mixture, iii) drying the cast mixture to form an amorphous hydrogel film, iv) seeding the cast mixture with a seed crystal of the crystallizable molecule, v) growing the crystallizable molecule into a crystal structure within the uncrosslinked polymer, vi) exposing the cast mixture to ultraviolet light, wherein the exposure results in a gelling or a crosslinking of the polymer, vii) crosslinking the uncrosslinked polymer around the crystal structure by an addition of one or more crosslinking agents under conditions in which the crystal structure within the crosslinked polymer is maintained, viii) removing the one or more crystals of the crystallizable polymers by rinsing with water to form the porous hydrogel, and ix) removing water from the porous hydrogel by controlled dessication under pressure. In one aspect the composition is administered prior to, during or after the surgery The present invention in one embodiment provides a method of making a directionally networked porous anti-adhesion hydrogel comprising the steps of: (i) preparing an aqueous mixture comprising hyaluronic acid, alginic acid, and urea, (ii) casting the aqueous mixture onto a vessel, a slide, a plate, tissue-culture dish or combinations and modifications thereof to form a cast mixture, (iii) drying the cast mixture to form an amorphous hydrogel film, (iv) seeding the cast mixture with one or more urea crystals, (v) growing the urea into a crystal structure within the uncrosslinked alginate, (vi) exposing the cast mixture to ultraviolet light, wherein the exposure results in a gelling or a crosslinking of the alginate, (vii) removing the one or more urea crystals by rinsing with water to form the porous hydrogel, and (viii) removing water from the porous hydrogel by controlled dessication under pressure.

The method described hereinabove comprises the optional steps of: surface modifying the hydrogel with hyaluronic acid by soaking the dessicated hydrogel in an aqueous solution of the hyaluronic acid in a presence of EDC/NHS and crosslinking the uncrosslinked alginate around the urea crystal structure by an addition of calcium chloride under conditions in which the urea crystal structure within the crosslinked alginate is maintained. In one aspect the method comprises the optional step of encapsulating one or more agents selected from drugs, growth factors, hormones, proteins or combinations thereof in the one or more pores or the matrix of the porous hydrogel. In another aspect the hydrogel prevents tissue adhesion following surgery, promotes wound healing, delivers drug or growth factors to the support healing, inhibits or prevents infiltration of blood, blood protein, fibroblasts, and inflammatory responses in the surgical site.

Another embodiment of the instant invention relates to a method for making a bilayer biofunctionalized HA-based film comprising the steps of: providing a first layer and a second layer, wherein the first layer and the second layer are made by a method comprising the steps of: (i) preparing an aqueous mixture comprising hyaluronic acid, alginic acid, and urea, (ii) casting the aqueous mixture onto a vessel, a slide, a plate, tissue-culture dish or combinations and modifications thereof to form a cast mixture, (iii) drying the cast mixture to form an amorphous hydrogel film, (iv) seeding the cast mixture with one or more urea crystals, (v) growing the urea into a crystal structure within the uncrosslinked alginate, (vi) exposing the cast mixture to ultraviolet light, wherein the exposure results in a gelling or a crosslinking of the alginate, (vii) removing the one or more urea crystals by rinsing with water to form the porous hydrogel, and (viii) removing water from the porous hydrogel by controlled dessication under pressure and fusing the first layer and the second layer to form the bilayer biofunctionalized HA-based film. In one aspect the first layer is a directionally networked porous anti-adhesion hydrogel. In another aspect the second layer is a directionally networked porous hydrogel, wherein the second layer promotes cell adhesion or cell infiltration. In yet another aspect the method comprises the optional step of covalently immobilizing one or more peptides, proteins, growth hormones or growth factors on the second layer. In another aspect the peptide is an Arginine-Glycine-Aspartic Acid (RGD) peptide. In another aspect the bilayer biofunctionalized HA-based film is used as a nerve wrap, a dural replacement, a skin graft, for promoting bone in-growth in fracture dressing, chronic wound repair, and patch cardiac or pulmonary tissues to facilitate tissue repair.

In yet another embodiment the present invention discloses a composition for a nerve wrap, a dural replacement, a skin graft, for promoting bone in-growth in fracture dressing, chronic wound repair, patch cardiac or pulmonary tissues to facilitate tissue repair or combinations thereof comprising a bilayer biofunctionalized HA-based film, wherein the film is made by a method comprising the steps of: providing a first layer and a second layer, wherein the first layer and the second layer are made by a method comprising the steps of: preparing an aqueous mixture comprising hyaluronic acid, alginic acid, and urea, casting the aqueous mixture onto a vessel, a slide, a plate, tissue-culture dish or combinations and modifications thereof to form a cast mixture, drying the cast mixture to form an amorphous hydrogel film, seeding the cast mixture with one or more urea crystals, growing the urea into a crystal structure within the uncrosslinked alginate, exposing the cast mixture to ultraviolet light, wherein the exposure results in a gelling or a crosslinking of the alginate, removing the one or more urea crystals by rinsing with water to form the porous hydrogel, and removing water from the porous hydrogel by controlled dessication under pressure and fusing the first layer and the second layer to form the bilayer biofunctionalized HA-based film. In one aspect the composition is administered by an injection, inserted or placed during, after, or prior to a surgical procedure or is applied directly to an affected area.

BRIEF DESCRIPTION OF THE DRAWINGS

For a more complete understanding of the features and advantages of the present invention, reference is now made to the detailed description of the invention along with the accompanying figures and in which:

FIG. 2A fluorescent biotinylated HA crosslinked to surface labeled with FITC/Neutravadin. When not crosslinked, biotinylated HA washed away (4×), FIG. 2B is a glass slide for FIG. 2A, FIG. 2C is a SEM of the surface-modified film cross-sectional surface indicating pores filled, scale bar 2 μm, and FIG. 2D is a SEM of a templated film, no surface modification, cross-sectional surface indicating unfilled porous, scale bar 1 μm;

FIG. 3A pulling in tension, FIG. 3B crumpling and squeezing, and FIG. 3C returning to original geometry with no tearing or compromise of integrity;

FIGS. 4A and 4B show the ASTM D638 tensile testing of: FIG. 4A urea patterned alginate/HA film and FIG. 4B alginate/HA film with no patterning;

FIG. 5A linear patterning with 4% urea, 5" by 5" film, and FIG. 5B radial patterning with 6% urea, 3" by 3" film;

FIGS. 8A and 8B are plots showing the results of the wet sample degradation studies that were conducted at 37° C. in: FIG. 8A PBS or FIG. 8B 50 IU/mL of hyase. Dashed lines are representative of an estimated degradation since small bits can be seen visually for the duration of the study; and FIGS. 9A-9E show human dermal fibroblast cells (P=3) were cultured on: FIG. 9A a PLL substrate, FIG. 9B on alginate film, FIG. 9C on alginate/modified HA film or FIG. 9D alginate/modified HA film with HA surface modification, FIG. 9E is a plot of the % cell adhesion on the different substrates described in FIGS. 9A to 9D.

DETAILED DESCRIPTION OF THE INVENTION

Figure 1:
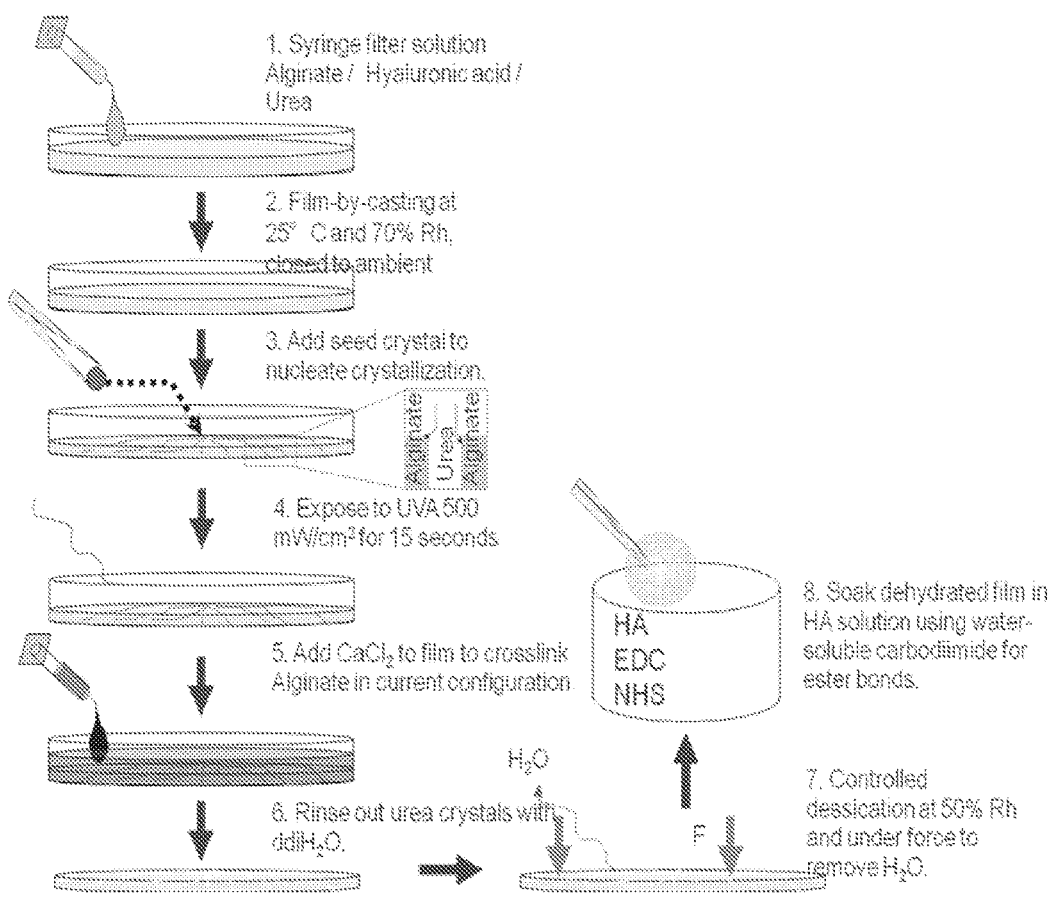
FIG. 1 is a schematic showing the techniques for fabricating the crystal-templated biopolymer hydrogels of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The instant invention describes a non-toxic anti-adhesion hydrogel barrier, particularly a barrier composed of non-synthetic, hydrophilic, biodegradable, biocompatible polysaccharides formed by constructing a unique interpenetrating, crosslinked network with a unique porosity, and also a method for preparing the same. The hydrogel barrier described herein solves the problems of a film, bulk sponge or nonwoven type anti-adhesion system, including adhesion to tissue or organs, physical strength, in vivo reposition flexibility, ease of handling (i.e., bending, folding, cutting, rolling, manipulating), and appropriate degradation timing.

The highly hydrophilic, non-synthetic nature of the barrier of the present invention selectively inhibits fibroblast infiltration into a surgical microenvironment and because of its local anti-adhesive properties the barrier does not inhibit wound healing. The barrier of the present invention does not tear, break or stick to itself when folded or rolled and can be easily handled when using surgical instruments lending its use in a variety of operations.

The unique features of the present invention are: (i) the barrier is comprised of tunable biopolymers for controllable mechanical robustness and degradation, (ii) barrier effectively reduces unwanted adhesions using non-synthetic components, and (iii) barrier has unique, controlled hierarchical porosity that can be backfilled with a variety of materials that may also be charged with small molecules (drugs, growth factors) to further inhibit unwanted response or to support healthy wound healing. No other technology has this combination of features.

The unique benefits provided by the barriers described herein are (i) improved handling characteristics, for example the barrier is easily folded, cut, sutured, manipulated in biologically relevant conditions, (ii) persistence in desired area throughout healing duration, (iii) improved in vivo repositioning flexibility, and (iv) unique porous structure that exhibits a tunable release profile for material, small molecules or growth factors.

No other methods in literature are similar to the technique presented herein. Current anti-adhesion technologies are described herein below U.S. Pat. No. 6,599,526 discloses a pericardial anti-adhesion patch comprising a collagenous material and a non-living cellular component for preventing adhesion during surgery. U.S. Pat. No. 6,566,345 discloses anti-adhesion compositions in the form of a fluid, gel or foam made of intermacromolecular complexes of polysaccharides such as carboxyl-containing polysaccharides, polyethers, polyacids, polyalkylene oxides, etc., and synthetic polymers. Korean Patent Publication No. 2003-0055102 discloses an anti-adhesion barrier for preventing inflammation and healing wounds comprising carboxymethylcellulose (CMC) and gellan gum. But, the anti-adhesion barriers in the form of a gel, fluid, foam, etc., are not accurately fixed at the wound site; they move downward because of gravity and, thus, are less effective in healing wounds and reducing adhesion.

European Patent No. 092,733 discloses anti-adhesion barriers in the form of a membrane, gel, fiber, nonwoven, sponge, etc. prepared from crosslinking of carboxymethylcellulose (CMC) and polyethylene oxide (PEO). However, carboxymethylcellulose is less biocompatible than bio-originated materials. Since polyethylene glycol or other synthetic polymers are not biodegradable, only materials having a small molecular weight that are capable of being metabolized can be used. However, since materials having a small molecular weight are absorbed quickly, the role of the anti-adhesion barrier cannot be sustained sufficiently.

U.S. Pat. No. 6,133,325 discloses membrane type anti-adhesion compositions made of intermacromolecular complexes of polysaccharides and polyethers. Korean Patent Publication No. 2002-0027747 discloses that a water-soluble polymer gel prepared from alternating copolymerization of a block copolymer of p-dioxanone and L-lactide with polyethylene glycol (PEG) can be utilized as an anti-adhesion barrier, drug carrier, tissue adhesive, alveolar membrane, etc. But, this gel type anti-adhesion barrier is also problematic in accurately fixing at wound sites as the abdominal internal organs or tissues are constantly moving. U.S. Pat. No. 6,630,167 discloses an anti-adhesion barrier prepared from crosslinked hyaluronic acid. Since hyaluronic acid is a polysaccharide found in animal and human tissues, it has superior biocompatibility. However, in an unmodified form, hyaluronic acid is degraded quickly, with a half life of only 1 to 3 days. This method in particular claims a croslinking agent concentration of 10 to 80%, by weight, which is significantly greater than the 1% used in the presented technology. Crosslinking agents can be toxic at high concentrations and removing large concentrations of cros slinking agents can be difficult.

U.S. Pat. No. 6,693,089 discloses a method of reducing adhesions using an alginate solution and Korean Patent Publication No. 2002-0032351 discloses a semi-IPN (semi-interpenetrating network) type anti-adhesion barrier using water-soluble alginic acid and CMC, in which alginates are selectively bound to calcium ions. However, these patents include ionically crosslinked alginate by calcium, which, when degraded quickly, releases a bulk charge of calcium ions into the surrounding tissues, further aggravating injured tissues. There is also the problem of non bio-material uses.

There are publications regarding the treatment of cellulose acetate with siloxane. But, since celluloses are sensitive to pH, there is a difficulty in processing them. Also, although they are natural polymers, celluloses are not a constituent of the human body and are known to have the potential to cause a foreign body reaction. Furthermore, there remains the task of modifying their structure, e.g., through oxidation, so that they can be hydrolyzed inside the body.

Anti-adhesion barriers that are currently on the market are in the form of a film, sponge, fabric, gel, solution, etc. In general, the film or sponge type is easier to fix at a specific site than the solution or gel type. Interceed™ from Johnson & Johnson is the first commercialized anti-adhesion barrier. It is a fabric type product made of ORC and adheres tightly to highly irregular organs or tissues. But, as mentioned earlier, ORC is a non-bio-oriented material and has poor biocompatibility. Also, because of a very large pore size, cells or blood proteins may easily penetrate the barrier, and the anti-adhesion barrier is deformed by external force during handling. Seprafilm is a film type anti-adhesion barrier made of HA and CMC by Genzyme Biosurgery. Seprafilm tends to roll when in contact with water and to be brittle when dry. Thus, wet hands have to be avoided and moisture should be minimized at the surgical site, which can be very difficult.

HYDROSORB SHIELD® from MacroPore Biosurgery Inc., which is used for adhesion control in certain spinal applications, or SURGI-WRAP™ from Mast Biosurgery, USA which is used after open surgery, are transparent film type anti-adhesion barriers made of poly(L-lactide-co-D,L-lactide) (PLA, 70:30), a biodegradable polymer. With a long biodegradation period of at least 4 weeks and superior mechanical strength, they are known as easy-to-handle products. Films made of PLA or poly(glycolic acid) (PGA) are easy to roll to one side, but they do not adhere well to the three-dimensionally, highly irregular surfaces of organs or tissues. Also, since these materials are hydrophobic, they do not absorb moisture well, and, therefore, do not adhere well to the wet surface of organs or tissues. Also, when hydrolyzed in the body, these materials release acidic degradation products, which may cause further inflammation and adhesion. DuraGen® and DuraGen Plus® from Integra LifeSciences is a sponge type anti-adhesion barrier made of collagen from an animal source, which has been developed for surgery and neurosurgery. Since the collagen sponge absorbs moisture, it readily adheres to the surface of organs. However, these barriers have relatively weak physical strength and, because of excessive moisture absorption, tends to be too heavy to handle or transport to another site.

In general, an anti-adhesion barrier has to satisfy the following requirements: i) infiltration or attachment of cells or blood should be avoided through precise control of pore size or use of materials non-adherent to blood or cells, ii) the anti-adhesion barrier should be able to be attached at the desired site for a specified period of time, iii) a foreign body reaction should be minimized to reduce inflammation, which is the cause of adhesion, iv) the biodegradation period should be able to be controlled, so that the barrier capacity can be sustained for a requisite period of time, v) the anti-adhesion barrier should be flexible and have superior mechanical properties, including tensile strength and wet strength, for ease of handling during surgery, and vi) there should be no deformation for a necessary period of time, because the wound should be covered exactly.

Post-surgical adhesions tether tissues that should remain separate. Adhesions result from impaired autologous natural immune response. Surgical adhesions continue to plague the recovery period, with current technologies falling short of adhesion prevention. Incidence of adhesions following surgery is 80% (Yeo, 2007) resulting in chronic pain, limited motion, organ dysfunction, and even death (Cui et al., 2009). The healthcare costs associated with this are over $3.45 billion, annually (Wiseman, et al., 2010). Current approaches for preventing adhesions include better surgical practices (Holmdahl et al., 1997) (for e.g., powder free gloves, laparoscopic procedures, and reduction of dessication), biocompatible barrier devices (for e.g., polymer solutions, in situ crosslinkable hydrogels, pre-formed membranes), and pharmacotherapy agents like steroidal anti-inflammatory drugs (Dexamethasone; progesterone; hydrocortisone; prednisone), non-steroidal anti-inflammatory drugs (Ibuprofen; flurbiprofen; indomethacin; tolmetin; nimesulide), inhibitors of proinflammatory cytokines (Antibodies to transforming growth factor (TGF)-b1), antihistamine (Diphenhydramine; promethazine), free radical scavengers (Melatonin; vitamin E; superoxide dismutase), Anticoagulants (heparin), proteolytic agents (tissue-type plasminogen activator; streptokinase; urokinase; pepsin; trypsin; Neurokinin 1 receptor antagonist), and antiproliferative agents (mitomycin).

The most effective anti-adhesion barrier on the market reduces adhesion formation by only 50%. Many products are based on synthetic materials because of superior handling capabilities and low manufacturing costs. However, these synthetic materials are rendered ineffective in the presence of blood or blood proteins. The invention presented herein addresses the problems listed above and provides an effective method of blocking the infiltration of unwanted inflammatory response while maintaining robust mechanical properties for surgical handling. Because the present invention is constructed of natural materials, the risk of further aggravation is minimized, while blood and blood proteins will not adhere. Barriers on the market made from natural materials also degrade too quickly, allowing for adhesion formation. The present technology has a tunable degradation rate so that the barrier persists during the healing process.

Current products on the market that are most effective have poor handling properties. They are brittle when dry and are rendered inapplicable when wet. In an OR environment, a suitable solution would be able to maintain mechanical integrity when wet. The present invention offers superior handling properties when wet including in vivo repositioning capabilities and suturability.

The present invention describes the development of composite, dual-functioning materials to be placed at the interface between healing tissues and the surrounding tissues. The invention improves upon anti-adhesive biomaterial barriers, to aid in wound healing, and to modulate the inflammatory response. The present inventors have develop and characterize anti-adhesive HA-based material (biocompatible, non-immunogenic, non cell-adhesive, inhibits protein absorption, mechanically stable, cost effective, clinically sized, and appropriate degradation rate). In addition the present inventors have developed a bilayer biofunctionalized HA-based film that is biocompatible, bioabsorbable, non-immunogenic, dual functioning, regenerative, anti-adhesive, mechanically stable, cost effective, and clinically sized. Finally, they develop an injectable solution version of anti-adhesive film that is biocompatible, effective at reducing adhesions, encapsulates ibuprofen or tranexamic acid and has tunable release rates.

Hydrogels are generally polymer chain networks that are water-insoluble, but that absorb water. Often described as being "superabsorbent," hydrogels are able to retain up to 99% water and can be made from natural or synthetic polymers. Often, hydrogels will have a high degree of flexibility due to their high water content. Common uses for hydrogels include: sustained drug release, as scaffolds (e.g., in tissue engineering), as a thickening agent, as a biocompatible polymer, in biosensors and electrodes and for tissue replacement applications. Natural hydrogels may be made from agarose, methylcellulose, hyaluronic acid (HA), and other naturally-derived polymers.

HA is a linear polysaccharide with repeating disaccharide units composed of sodium D-glucuronate and N-acetyl-D-glucosamine. This naturally occurring glycosaminoglycan is a component of skin, synovial fluid, and subcutaneous and interstitial tissues. HA is metabolically eliminated from the body, and plays a role in protecting and lubricating cells and maintaining the structural integrity of tissues. Anionic carboxylic groups immobilize water molecules giving HA its viscoelastic and anti cell-adhesive properties. HA has been used in a variety of material designs for the prevention of postsurgical tissue adhesion. HA has been used as a dilute solution, a crosslinked hydrogel, or combined with CMC into sheets. HA is biocompatible, bioabsorbable/non-immunogenic (non-animal), very non-cell adhesive, polyanionic, hydrophilic, antifibrotic (1% HMW HA, Massie, 2005), pro-angiogenic and has been shown to reduce adhesion formation in animals and humans (Zawaneh, 2008; Diamond, 2006; Wiseman, 2010; Rajab, 2010). HA is clinically used to reduce adhesions: Seprafilm®, most effective and widely used anti-adhesion barrier on the market.

Alginic acid is biocompatible, bioabsorbable/non-immunogenic (non-animal) (Skjak-Braek, 1992), very non-cell adhesive, polyanionic, hydrophilic, cost effective, abundant (brown seaweed), mechanically viable for handling/suturing in ionically crosslinked form, and is shown to be significantly effective at adhesion prevention in animal models (Namba, 2006; Cho, 2010a; Cho, 2010b).

Attributes of alginate that statistically alter mechanical properties: (i) grade (Purification), (ii) gulcuronate to mannuronate ratio (High M ratio is pond-grown, primarily leaves, High G is deep sea harvested, primarily stems), and (iii) molecular weight/viscosity. However, highly purified alginate is very expensive ~$100/g, lower grade (inexpensive) alginates are not tested for molecular weight or G:M ratio, and purification processes are not standardized.

Crystal templated hydrogels of alginate and HA were created by casting a droplet of solution containing a photocrosslinkable derivative of HA, a photocrosslinkable derivative of alginate with photoinitiator (PI) and urea (FIG. 1). The solvent is evaporated and a urea seed crystal is touched to the droplet to nucleate urea crystallization. After crystallization the alginate and HA are photocrosslinked by UV exposure. Alginate may be further crosslinked ionically and rinsed with water to remove the urea leaving behind an alginate/HA hydrogel templated with the pattern of the urea crystals. The hydrogel may then be dehydrated for further surface modification using crosslinking agents (such as water soluble carbodiimides in ethanol/deionized water mixtures).

The method for preparing the alginate/HA films as described in the present invention includes five steps: film casting, solvent evaporation, crystal growth, crosslinking, and rinsing. In the first step a syringe filter introduces a solution comprising alginate/GMHA/urea on a plate. The solution is then cast as a film at 25° C. at 70% relative humidity. Solvent evaporation is required to achieve the super-saturation conditions necessary for crystallization. Evaporation also greatly increases the biopolymer concentration and solution viscosity. The combination of high viscosity and hydrogen bonding suppresses spontaneous urea crystallization and facilitates super-saturation. Urea seed crystals are deposited on the tips of a fine pair of tweezers and is added to nucleate crystallization followed by exposure to UVA (500 mW/cm$^2$) for 15 secs. Crystal growth began immediately and produced long dendritic branches that extended from the center to the edge of the film. Within seconds the entire volume of the hydrogel films were filled with urea crystals. These crystals comprised the urea crystal template. The films may optionally be crosslinked by an addition of one or more cross linking agents (for example an ionic crosslinking solution like $CaCl_2$ is added to the film to crosslink the alginate). The urea crystals are then rinsed out with double distilled water. The film formed thus is subjected to controlled dessication under force to remove water at 50% relative humidity. The dehydrated film may be subjected to further surface modification by creating one or more ester or less hydrolysable bonds by a variety of techniques (got e.g., soaking in a HA solution using water soluble carbodiimide for ester bonds).

Alginate films alone degraded too quickly in chelating environment. Calcium ions chelated by multiple salts and can degrade within a few hours. (Islam, 2010). Adding GMHA decreases degradation, but without compromising the mechanical strength provided by alginate.

Alginate film, alone, is too brittle and breaks with little manipulation. Adding urea introduces micron-sized pores which provide flexibility because spaces accept forces first.

Figures 2A, 2B:
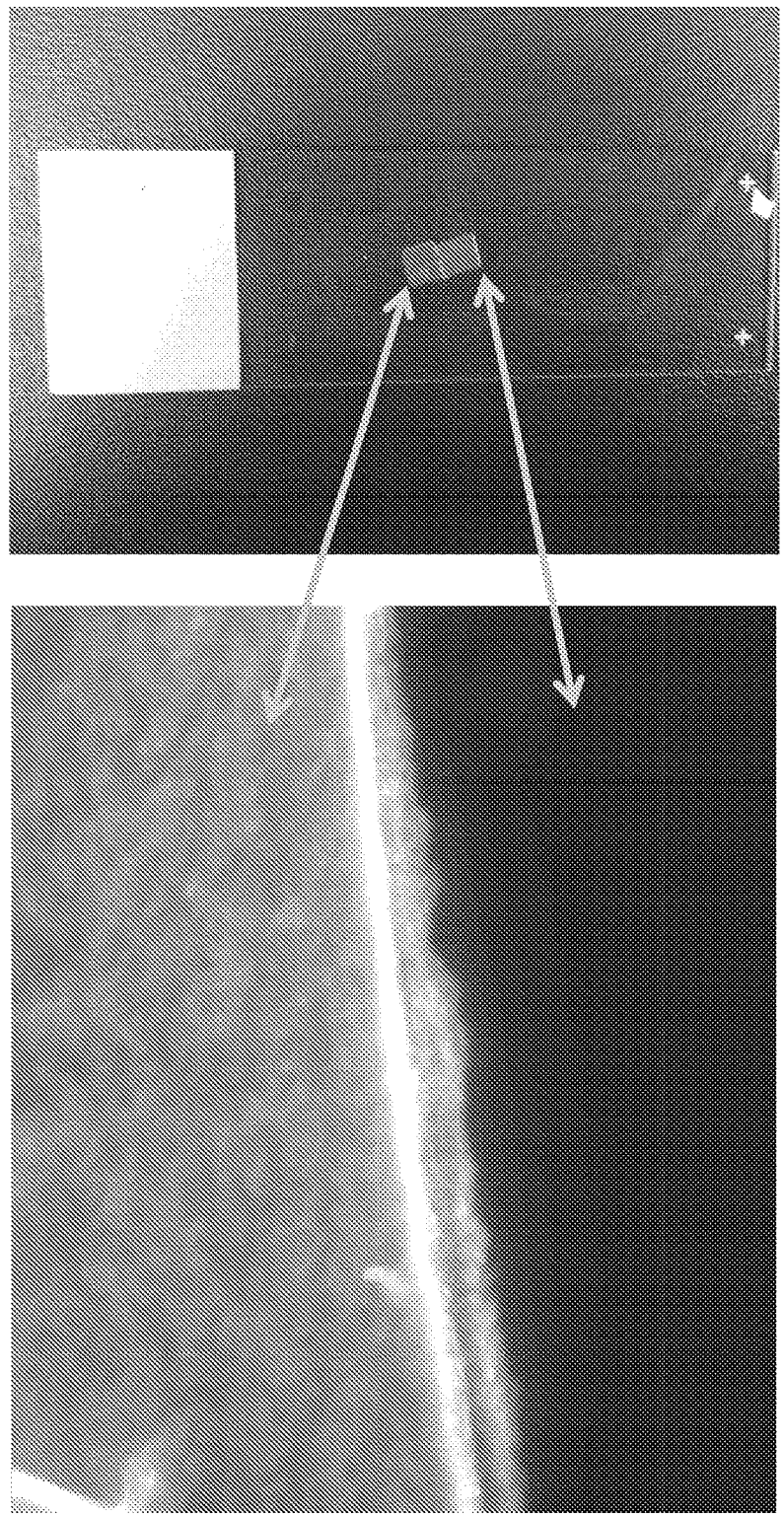
FIGS. 2A-2D show the surface modification of templated alginate films.
Figure 2C:
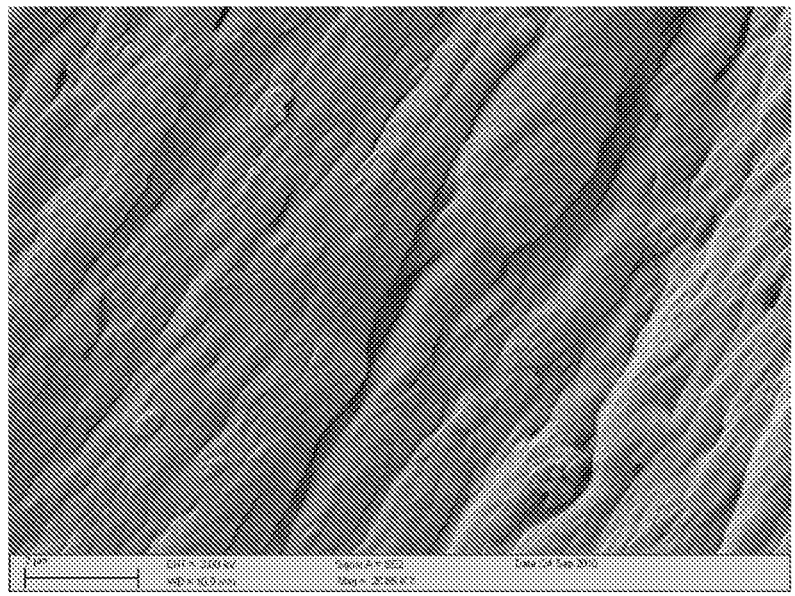
Figure 2D:
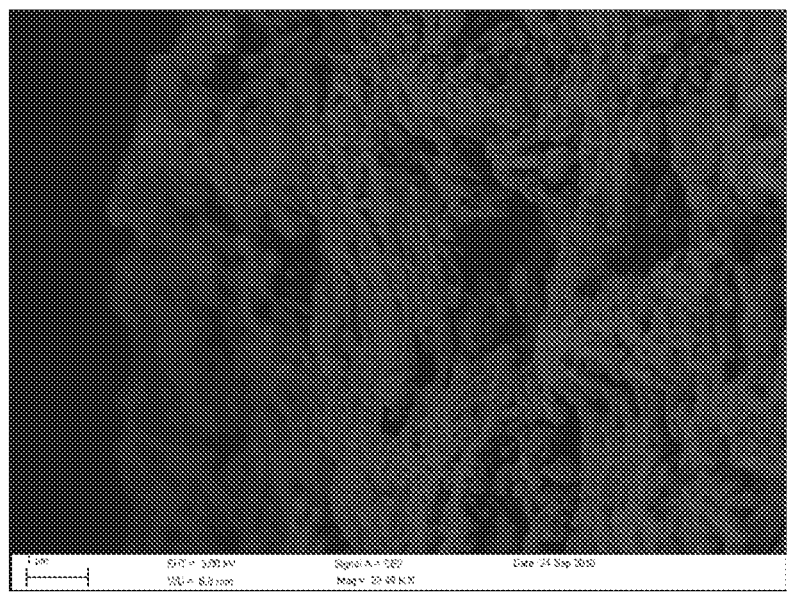

FIGS. 2A-2D show the surface modification of templated alginate films. FIG. 2A shows fluorescent biotinylated HA crosslinked to surface labeled with FITC/Neutravadin. When not crosslinked, biotinylated HA washed away (4×). FIG. 2B is a glass slide for FIG. 2A. FIG. 2C are is a SEM of the surface-modified film cross-sectional surface indicating pores filled, scale bar 2 μm and of a templated film, no surface modification, cross-sectional surface indicating unfilled porous, scale bar 1 μm, respectively.

Figure 3A:
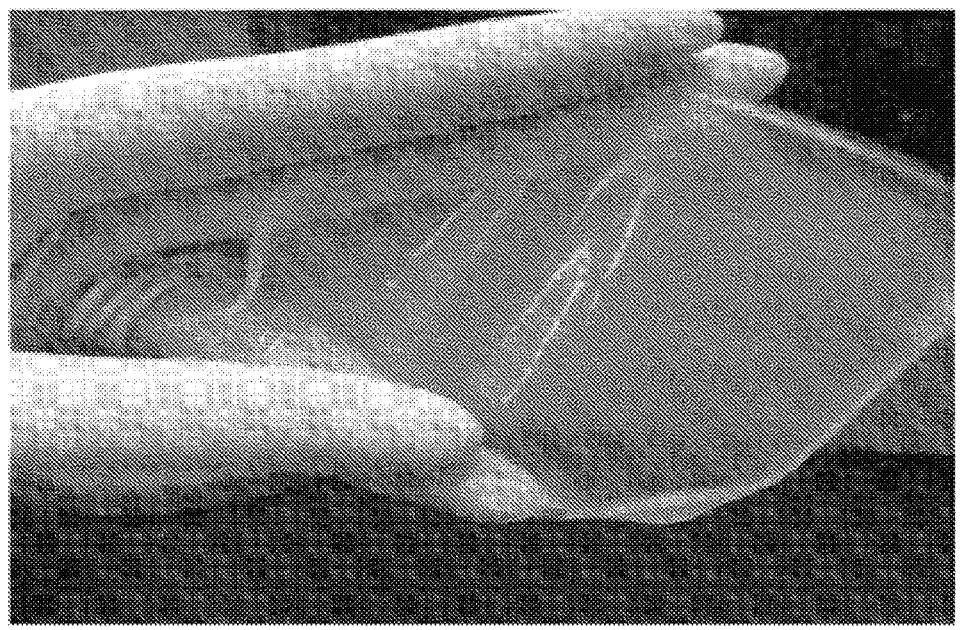
FIGS. 3A-3C show Alginate/HA film patterned with an urea crystallization pattern.
Figure 3B:
Figure 3C:
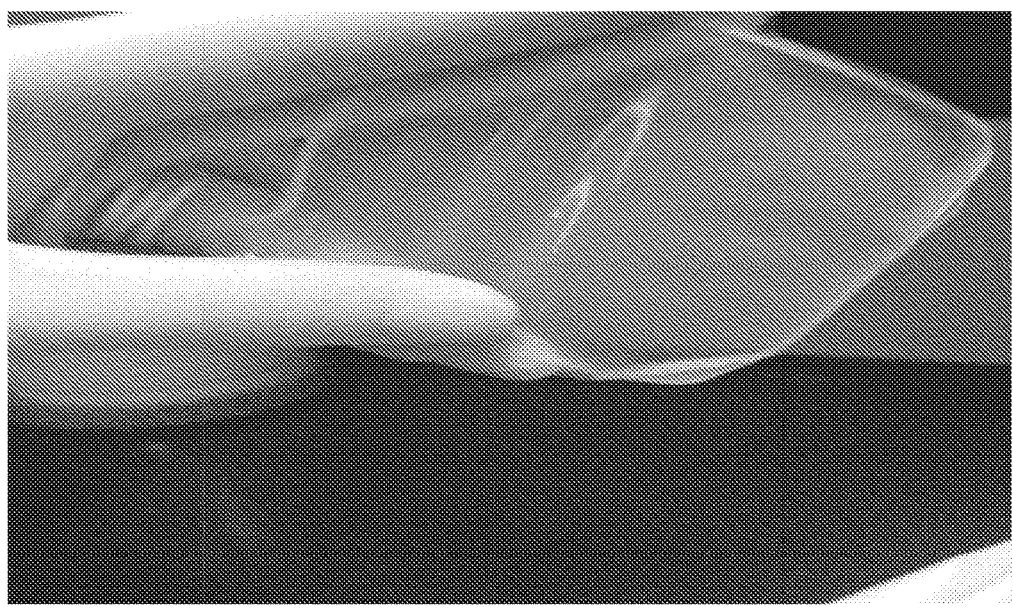

FIGS. 3A-3C are images showing the integrity of the Alginate/HA film patterned with an urea crystallization pattern, pulling in tension (FIG. 3A), crumpling and squeezing (FIG. 3B), and returning to original geometry with no tearing or compromise of integrity (FIG. 3C).

Figure 4A:
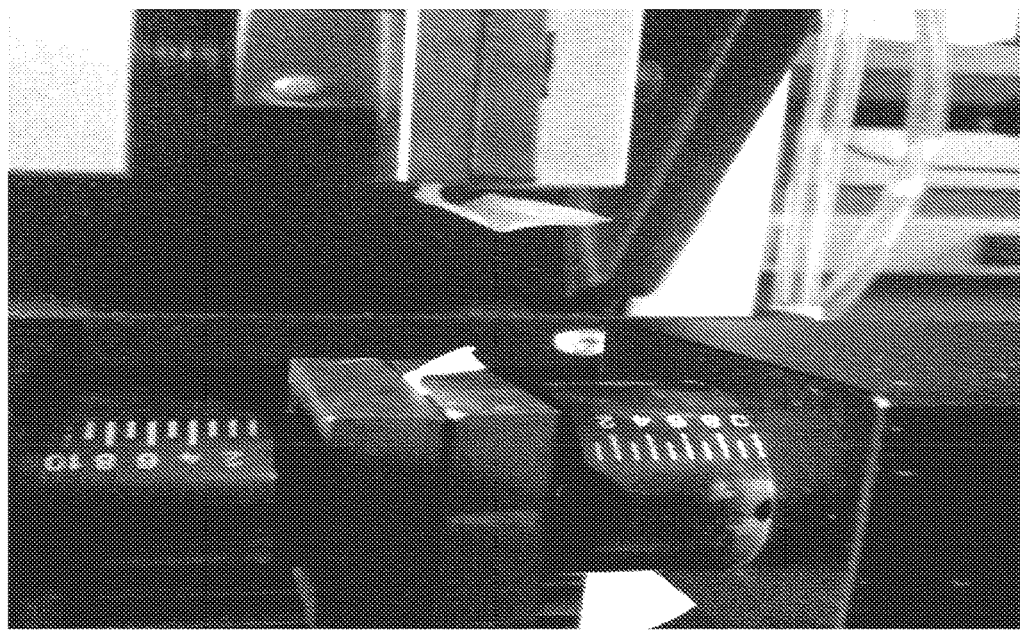
Figure 4B:
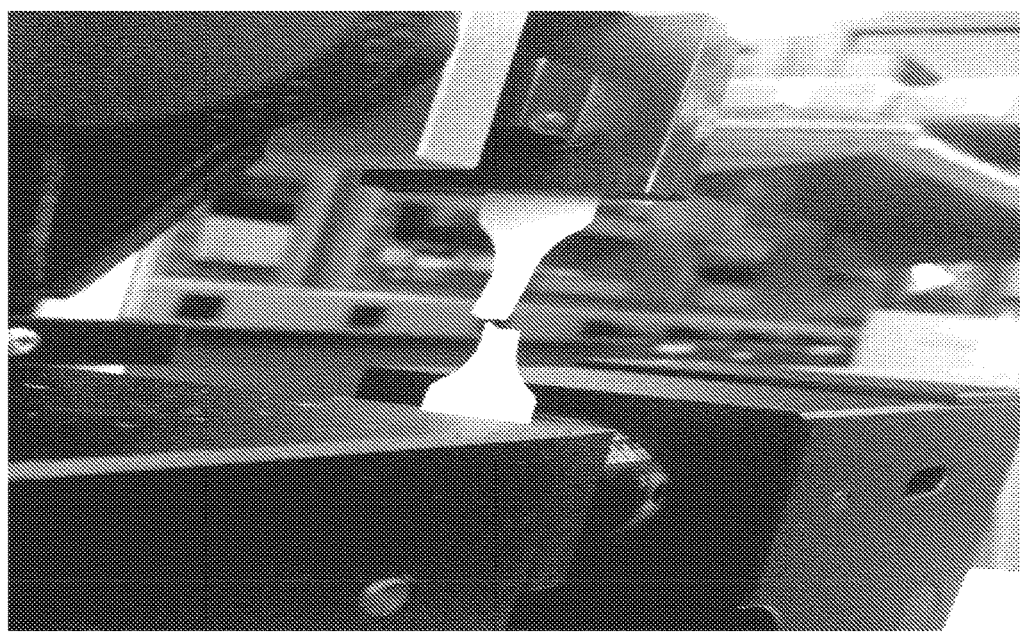
Figure 5A:
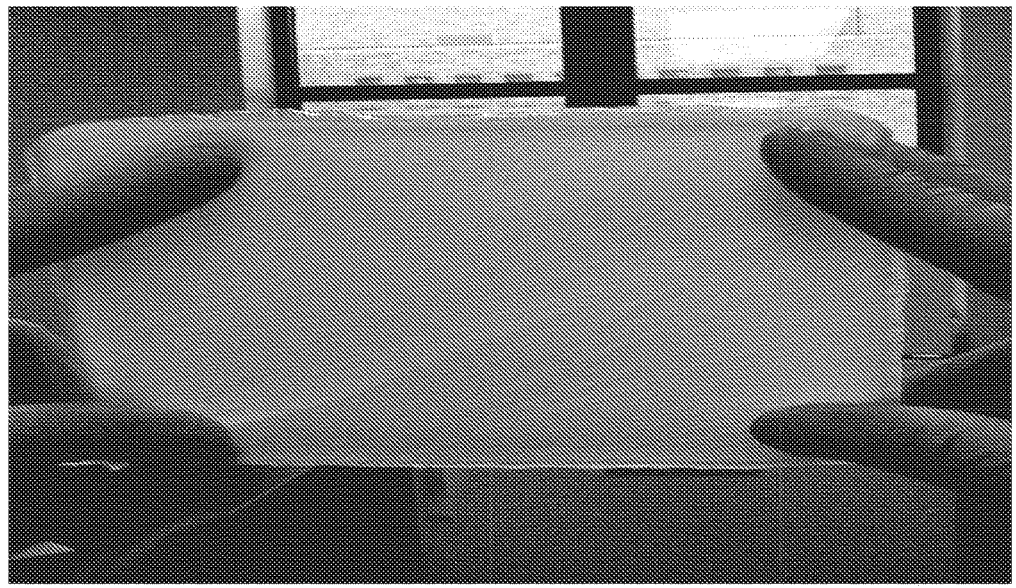
FIGS. 5A and 5B are examples of alginate/HA urea-templated films.
Figure 5B:
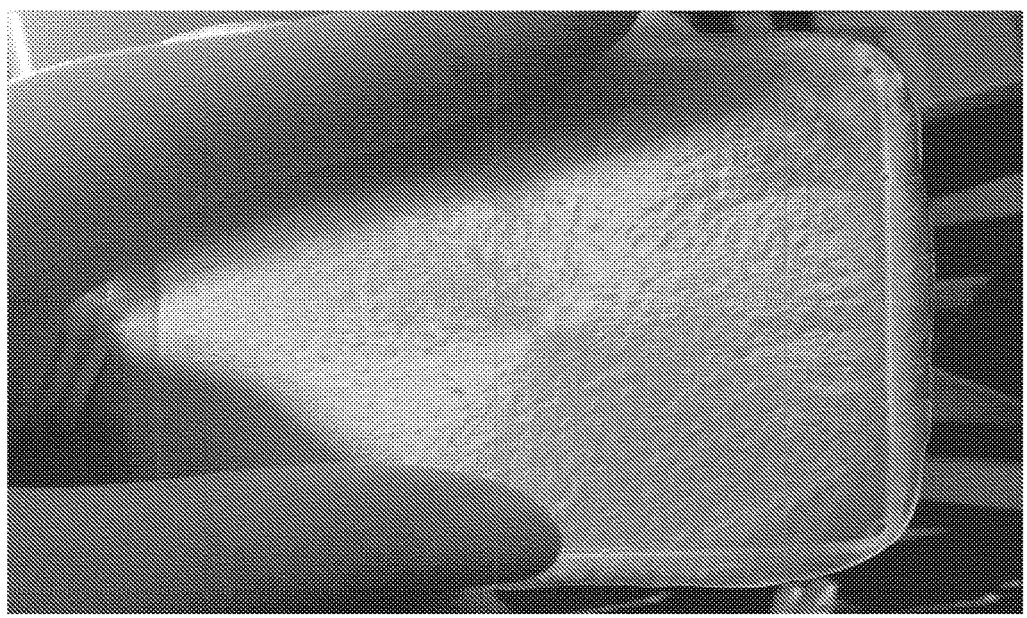

The ASTM D638 tensile testing of urea patterned alginate/HA film and alginate/HA film with no patterning is shown in FIGS. 4A and 4B. The patterned film recoils in response to plastic deformation before failure. The non-patterned film breaks with a brittle fracture. Examples of alginate/HA urea-templated films are shown in FIGS. 5A and 5B, linear patterning with 4% urea, 5" by 5" film (5A), and radial patterning with 6% urea, 3" by 3" film (5B).

Figure 6:
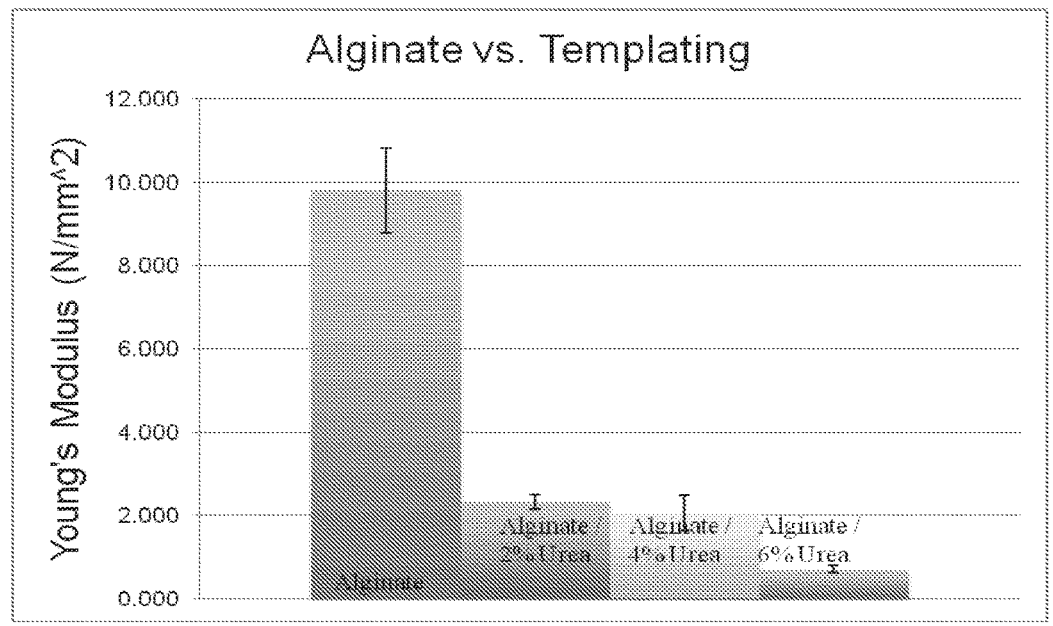
FIG. 6 is a plot showing the ASTM D638 tensile testing of alginate films with increased concentration of urea crystallization.
Figure 7:
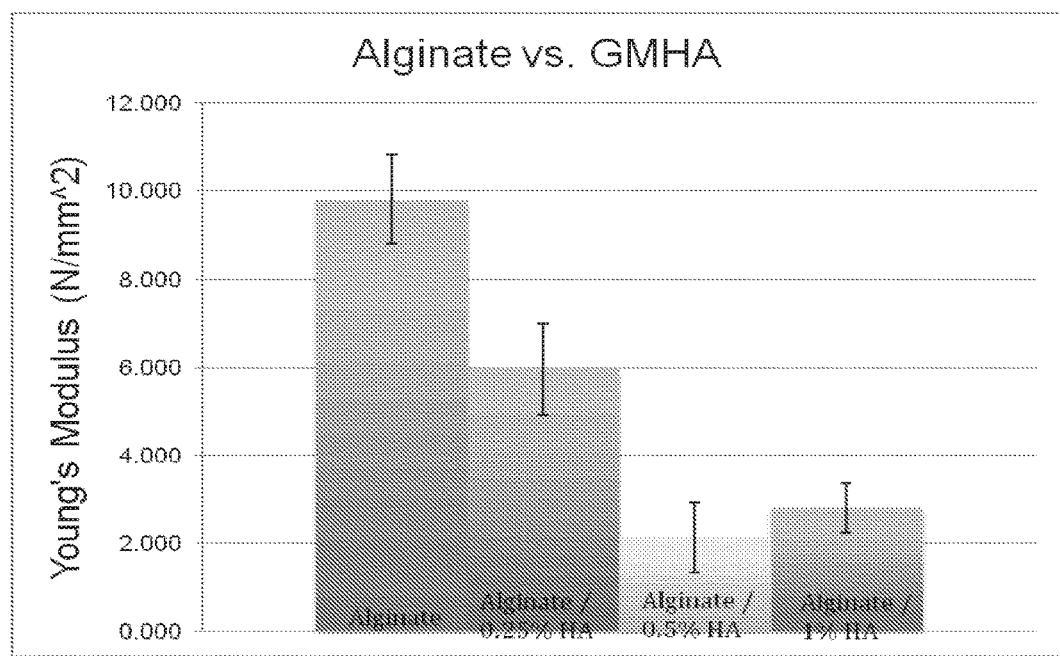
FIG. 7 is a plot showing the ASTM D638 tensile testing of alginate films with increased concentration of HA.

FIG. 6 is a plot showing the ASTM D638 tensile testing of alginate films with increased concentration of urea crystallization. The trend indicates increased plasticity with increased crystallization patterning. FIG. 7 is a plot showing the ASTM D638 tensile testing of alginate films with increased concentration of HA. The trend indicates decreased tensile strength with increased HA, until a critical point, where the concentration of HA improves the tensile strength by providing crosslinked strength.

Figure 8A:
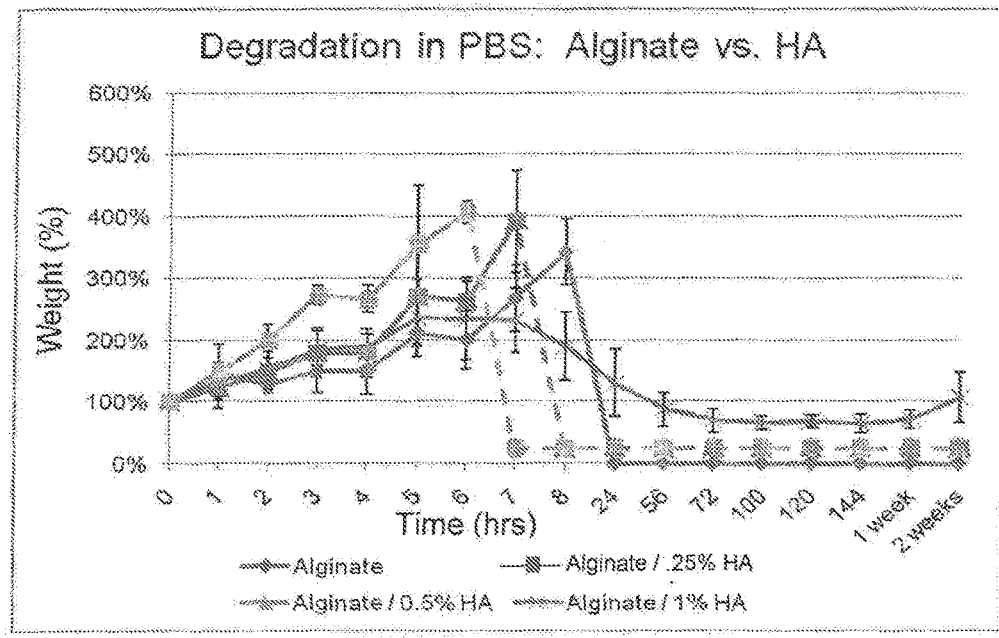
Figure 8B:
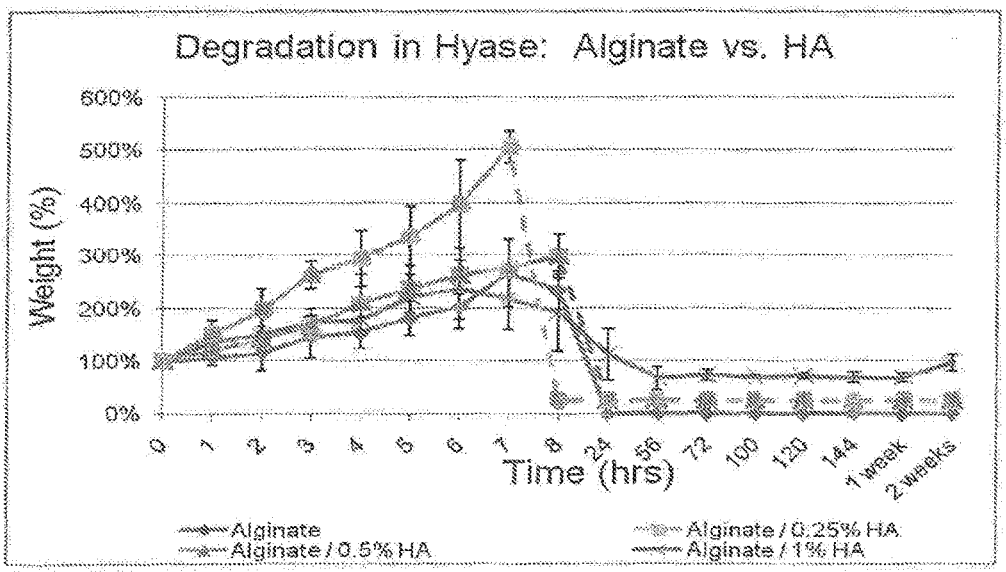

Characterization of synthesized Alginate/HA films: FIGS. 8A and 8B are plots showing the results of the wet sample degradation studies of an Alginate/HA film of the present invention conducted at 37° C. in PBS or 50 IU/mL of hyase, respectively. Briefly, the method involves determining a pre-test weight of the Alginate/HA film (or films) ($W_o$), after that the film is placed in PBS or the hyase at 37° C. and are removed at pre-defined time points and weighed ($W_f$). The procedure is repeated until the weight cannot be taken or the appropriate pre-defined end point time is reached. The degradation rate is calculated using the formula given below:

$$\% \text{ Weight Loss} = 100 \times (W_o - W_f)/W_o$$

Dashed lines are representative of an estimated degradation since small bits can be seen visually for the duration of the study. Alginate alone films degrade due to chelating agents in the buffer.

Figure 9E:
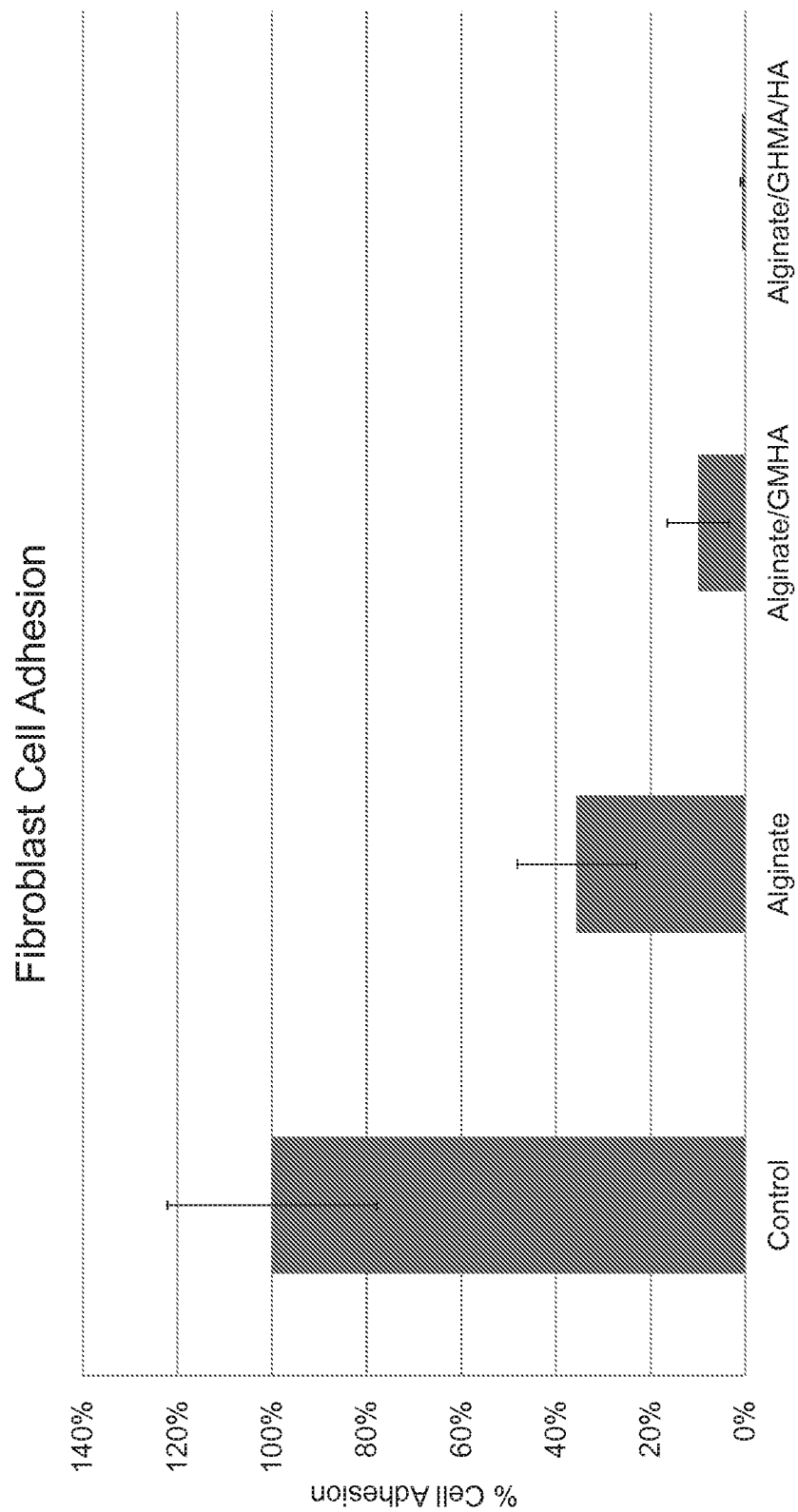

FIG. 9 is a schematic showing the steps involved in the evaluation of the anti-cell adhesion properties of an alginate/HA film of the present invention. A culture of fibroblast cells is taken, half of it is retained on a TCPS dish and the other half is retained on an Alginate/HA film that has been placed on a dish. After a 24 hour waiting period, both the dishes are stained with calcein/ethidium to label the live or dead cells. The cell adhesion or non cell adhesion is validated using one or more commonly used cell technologies.

To study cell adhesion properties human dermal fibroblasts cells (P=3) were cultured on a PLL substrate, on alginate film, on alginate/modified HA film or alginate/modified HA film with HA surface modification alginate/HA film of the present invention (FIGS. 9A-9D). A culture of fibroblast cells is taken and split in half and placed separately on two TCPS dishes. The film/substrate to be tested is placed on top of one of the dishes. After a 6 hour waiting period, both the dishes are stained with calcein/ethidium to label the live or dead cells. FIG. 9E is a plot of the % cell adhesion on the different substrates described in FIGS. 9A to 9D. Leaching studies showed no cytotoxic results from film, staining at 24 hours.

The barrier disclosed hereinabove possesses significant advantages over currently existing technologies: (1) the barrier has improved handling characteristics, is easily folded, cut, sutured, manipulated in biologically relevant conditions; (2) barrier persists in desired area throughout healing duration; (3) barrier has improved in vivo repositioning flexibility; and (4) unique porous structure that exhibits a tunable release profile for material, small molecules, or growth factors.

The unique anti-adhesive membrane described hereinabove could also be an innovative solution in the enormous wound care market. As a substrate for a non-adhesive, hydrophilic, yet absorbent wound dressing, the present invention can be used extensively in burn care, chronic non-healing wound care, and reconstructive plastic surgery.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An apparatus comprising:
   a translucent, desiccated, amorphous, non-synthetic, non-cytotoxic hydrogel film including:
   a first film layer comprising first uncrosslinked hyaluronic acid and first alginate, the first alginate being negatively charged and crosslinked with at least one first cation; and
   a second film layer comprising second uncrosslinked hyaluronic acid and second alginate, the second alginate being negatively charged and crosslinked with at least one second cation;

wherein (a) the first film layer is fused to the second film layer, (b) each of the at least one first and second cations includes calcium; (c) the first film layer is bonded to a surface coating comprising ester bonds and one biopolymer selected from the group consisting of collagen, chitosan, gelatin, and combinations thereof; (d) the composition of each of the first and second film layers is no less than 1% hyaluronic acid by dry weight and no greater than 33% hyaluronic acid by dry weight; and (e) at least one of the first and second film layers is adhesive to cells and another of the first and second film layers is anti-adhesive and non-attractive to cells.

2. The apparatus of claim 1, wherein the first hyaluronic acid and the first alginate are formed around a pore network.

3. The apparatus of claim 2, wherein the pore network is branched.

4. The apparatus of claim 1 wherein the hydrogel film is configured to prevent tissue adhesion following surgery.

5. The apparatus of claim 1, wherein the hydrogel film encapsulates at least one of a drug, growth factor, hormone, protein, and combinations thereof.

6. The apparatus of claim 1, wherein the hydrogel film is unpatterned.

7. The apparatus of claim 2, wherein the pore network includes channels comprising at least one of a drug, growth factor, hormone, protein, and combinations thereof.

8. The apparatus of claim 1, wherein the first film layer is anti-adhesive and non-attractive to cells and the second film layer is adhesive to cells.

* * * * *